US011786727B2

(12) United States Patent
Colborn et al.

(10) Patent No.: US 11,786,727 B2
(45) Date of Patent: Oct. 17, 2023

(54) REVERSE ELECTRODE CHARGING FOR NEUROSTIMULATION

(71) Applicant: Noctrix Health, Inc., Pleasanton, CA (US)

(72) Inventors: John Craig Colborn, Magnolia, TX (US); Andrew Witte, Palo Alto, CA (US); Shriram Raghunathan, Castro Valley, CA (US); Douglas Richard Jeffrey, Oakland, CA (US)

(73) Assignee: NOCTRIX HEALTH, INC., Pleasanton, CA (US)

( * ) Notice: Subject to any disclaimer, the term of this patent is extended or adjusted under 35 U.S.C. 154(b) by 0 days.

(21) Appl. No.: 17/969,982

(22) Filed: Oct. 20, 2022

(65) Prior Publication Data

US 2023/0122561 A1 Apr. 20, 2023

Related U.S. Application Data

(60) Provisional application No. 63/270,011, filed on Oct. 20, 2021.

(51) Int. Cl.
*A61N 1/02* (2006.01)
*A61N 1/04* (2006.01)
(Continued)

(52) U.S. Cl.
CPC ........... *A61N 1/3603* (2017.08); *A61N 1/025* (2013.01); *A61N 1/0456* (2013.01);
(Continued)

(58) Field of Classification Search
CPC .... A61N 1/3603; A61N 1/025; A61N 1/0456; H02J 7/00032; H02J 7/00712;
(Continued)

(56) References Cited

U.S. PATENT DOCUMENTS 5,069,211 A * 12/1991 Bartelt ............... A61N 1/36021
607/66
2010/0076533 A1* 3/2010 Dar ...................... A61N 1/0492
607/115

(Continued)

FOREIGN PATENT DOCUMENTS

WO WO-2017201525 A1 11/2017

OTHER PUBLICATIONS

"International Application Serial No. PCT/US2022/047245, International Search Report dated Feb. 24, 2023", 6 pgs.

(Continued)

*Primary Examiner* — Carl H Layno
*Assistant Examiner* — Anh-Khoa N Dinh
(74) *Attorney, Agent, or Firm* — SCHWEGMAN LUNDBERG & WOESSNER, P.A.

(57) ABSTRACT

A transcutaneous neurostimulation therapy system can include an electrostimulation electronics unit, including first and second neurostimulation output which can be respectively coupled to first and second neurostimulation skin electrodes, and the electrostimulation electronics unit can include or be coupled to a rechargeable battery. The transcutaneous neurostimulation therapy system can also include battery charging circuitry configured for being coupled via the first and second neurostimulation output terminals to the electrostimulation electronics unit for charging the battery of the electrostimulation electronics unit through the first and second neurostimulation skin electrodes.

21 Claims, 7 Drawing Sheets

(51) Int. Cl.
*A61N 1/36* (2006.01)
*H02J 7/00* (2006.01)

(52) U.S. Cl.
CPC ...... *H02J 7/00032* (2020.01); *H02J 7/00712* (2020.01); *H02J 2207/20* (2020.01)

(58) Field of Classification Search
CPC .. H02J 2207/20; A61B 5/4806; A61B 5/4836; A61B 5/024; A61B 5/02405; A61B 5/0533; A61B 5/11; A61B 5/4809; A61B 5/4812; A61B 5/4815; A61B 5/6891; A61B 5/6892; A61M 2021/0072; A61M 21/02; A61M 2230/06; A61M 2230/10; A61M 2230/42; A61M 2230/60; A61M 2230/65; A61M 37/0092; A61M 2021/0016; A61M 2021/0027; A61M 2021/0083; A61M 2205/18; A61M 2205/3553; A61M 2205/3561; A61M 2205/3569; A61M 2205/3584; A61M 2205/3592; A61M 2205/502; A61M 2205/70; A61M 2205/8206; A61M 2209/01; A61M 2210/06; A61M 2230/005; A61M 2230/14; A61M 2230/63; A61M 16/0688
See application file for complete search history.

(56) References Cited

U.S. PATENT DOCUMENTS

2014/0148871 A1* 5/2014 Southwell .......... A61N 1/36034
607/145
2017/0021172 A1* 1/2017 Perez .................. A61N 1/0476
2018/0154147 A1* 6/2018 Izvorski ............. A61N 1/36034

OTHER PUBLICATIONS

"International Application Serial No. PCT/US2022/047245, Written Opinion dated Feb. 24, 2023", 6 pgs.

* cited by examiner

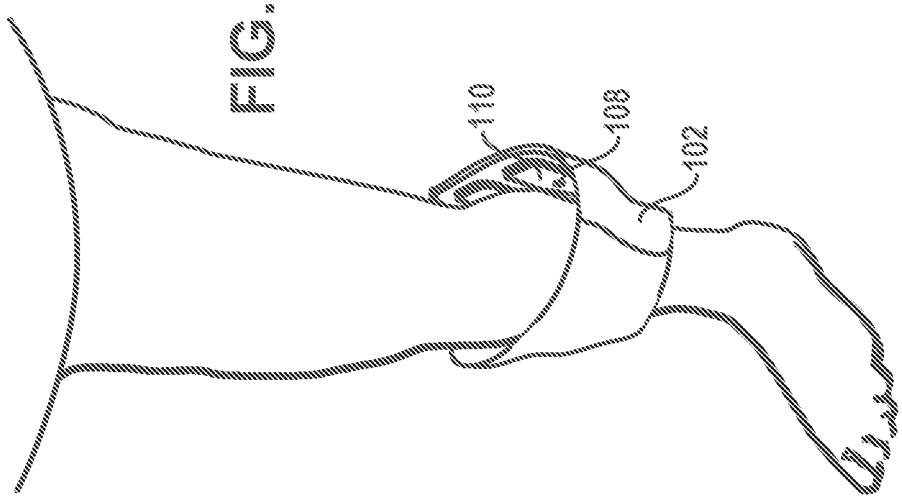
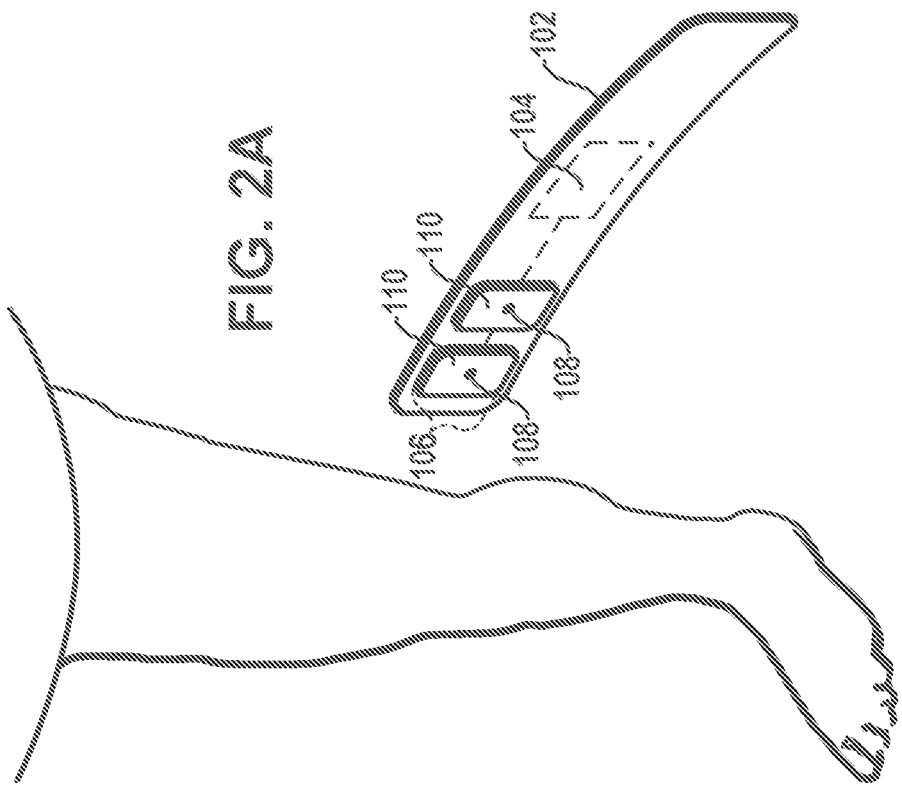

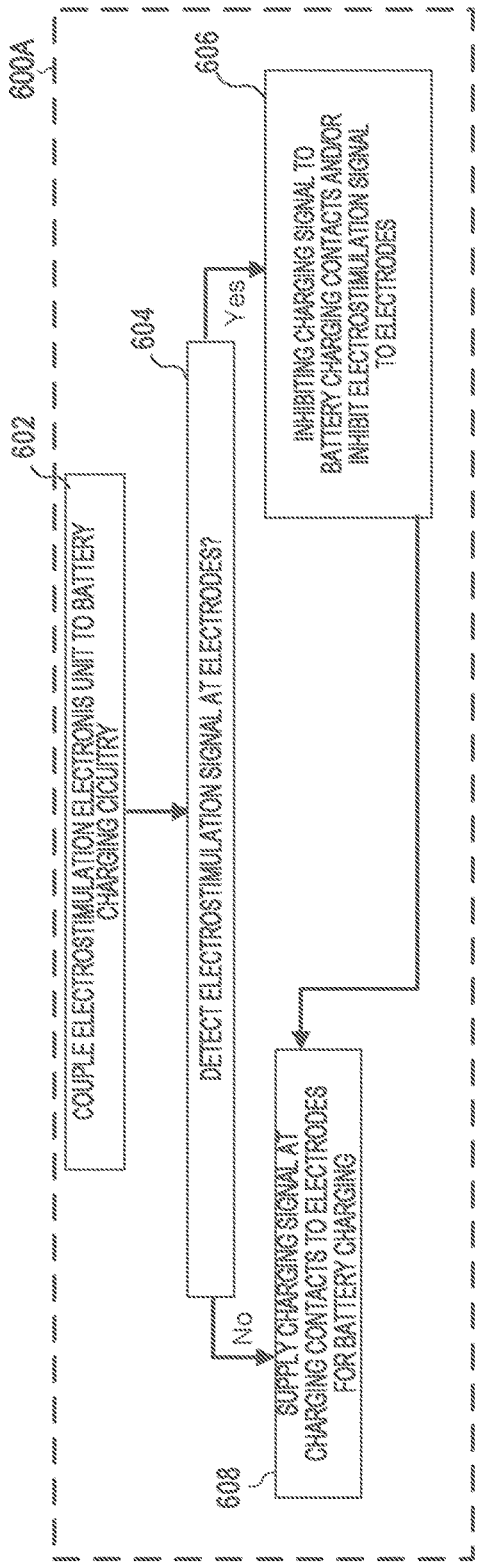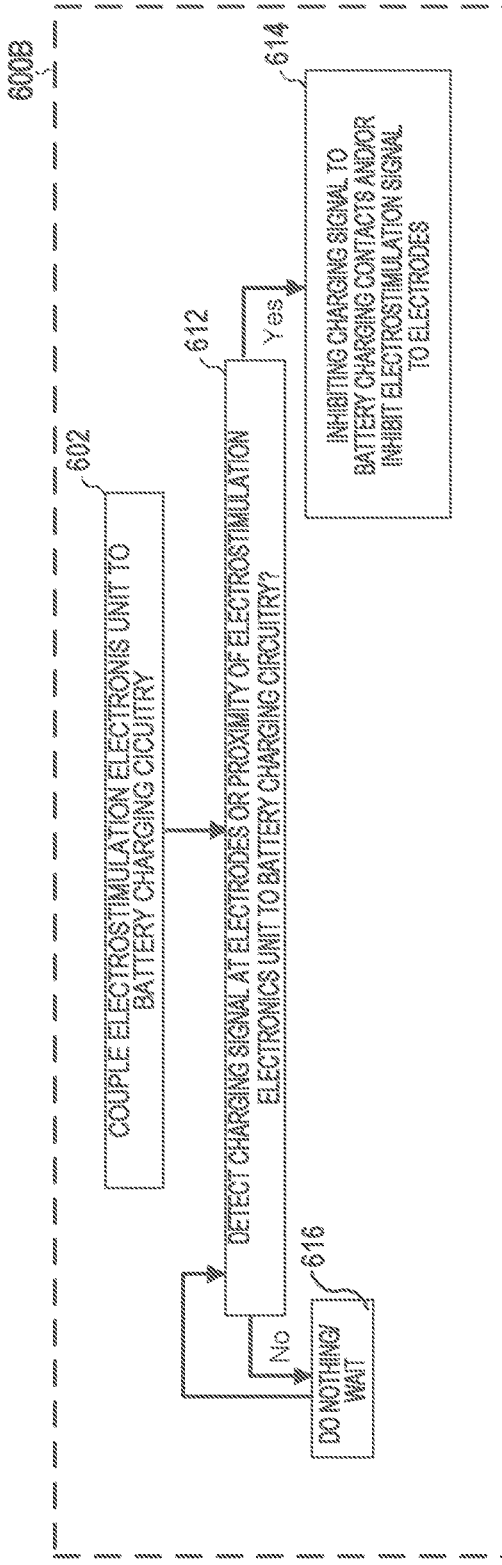

REVERSE ELECTRODE CHARGING FOR NEUROSTIMULATION

CLAIM OF PRIORITY

This application claims priority to U.S. Provisional Application Ser. No. 63/270,011, filed on Oct. 20, 2021, which is incorporated by reference herein in its entirety, and the benefit of priority of which is claimed herein.

TECHNICAL FIELD

This document pertains generally, but not by way of limitation, to neurostimulation devices, and more particularly to systems and methods for charging the devices for providing recurrent electrostimulation therapy sessions.

BACKGROUND

Skin surface electrodes are important components in many medical systems including, e.g., functional electrical stimulation (FES), electrocardiography (ECG), electromyography (EMG), electroencephalography (EEG), or electrooculography (EOG). The electrodes can provide transcutaneous delivery of electrical current or can act as transducers to measure, e.g., biopotentials for diagnostic testing. Several devices can provide medical treatment or therapy using skin surface electrodes in both clinical and home treatment environments.

SUMMARY

In several approaches using skin surface electrodes, an electrode pad can be used with an electrostimulation device for transcutaneous electrical contact with the body of a subject. The electrode pad can conduct electricity and can deliver an electrostimulation signal to skin of the subject. The electrostimulation device can generate the electrostimulation signal using energy stored onboard in a battery. As such, the battery can become depleted and must be recharged for recurrent use. The present inventors have recognized, among other things, the need for a neurostimulation therapy system with device charging capabilities that help enable maintenance and care of electrodes. The present inventors have also recognized employing device features for multiple functions, such as for both electrostimulation output and device charging, can improve efficiency and ease of performing electrostimulation in, e.g., home therapy sessions.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2A depicts an example of a wearable electrostimulation device in use with a subject.

FIG. 2B depicts an example of a wearable electrostimulation device in use with a subject.

FIG. 6A is a flowchart of an example of a transcutaneous neurostimulation therapy system.

FIG. 6B is a flowchart of an example of a transcutaneous neurostimulation therapy system.

DETAILED DESCRIPTION

Figure 1A:
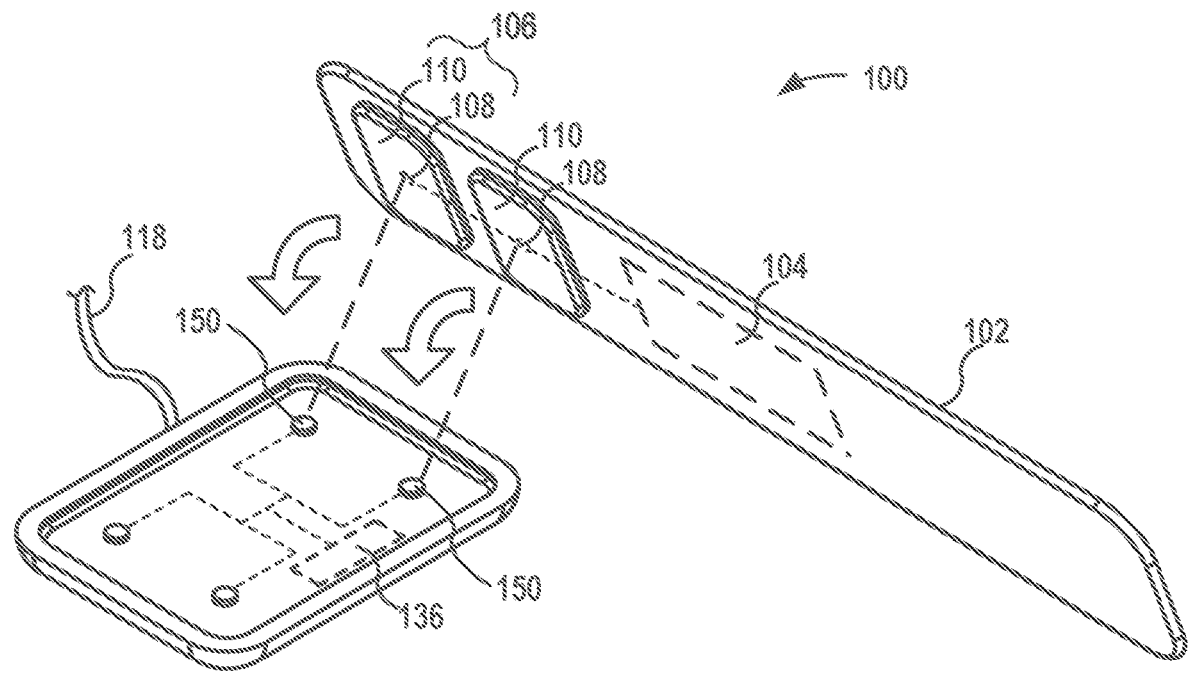
FIG. 1A depicts a perspective view of an example of a transcutaneous neurostimulation therapy system.

This document describes, among other things, to neurostimulation devices, and more particularly to systems and methods for charging the devices for providing recurrent electrostimulation therapy sessions. Skin surface electrodes can be used as a part of a medical system such as to perform a neurostimulation treatment or diagnostic procedure such as a part of a medical system for delivering electrical neurostimulation or recording electrical response activity.

For example, electrodes can be used with an electrostimulation device for delivering transcutaneous neurostimulation. Here, electrical impulses can be delivered from the electrodes such as to mimic or elicit a neural action potential. For example, the electrodes can include or use an electrode contact surrounded by an electrode pad such as a hydrogel. Reductions in moisture either through drying out or "fouling" of the hydrogel by dirt, skin oils, dander and other contaminants can result in reduced electrical conductivity and reduced adhesion. As such, the electrode pads should be carefully stored when not being used for electrostimulation and occasionally replaced in order to ensure proper electrode condition for electrostimulation. The electrostimulation device can also include or use a battery that can need charging while the device is not being used for electrostimulation. In one approach the electrode pads and the battery can be removed from the electrostimulation device and placed in a storage container and a battery charger, respectively. A challenge with this approach is that the electrostimulation device must be reassembled following electrode pad storage and battery charging before subsequent use. Further, it is challenging to incorporate dedicated battery charging features on the device for concurrent battery charging and electrode pad storage where device disassembly is not required.

The present disclosure relates to, among other things, systems and methods enabling concurrent battery charging and electrode pad storage. The present disclosure also relates to a neurostimulation therapy system with reverse device charging through two or more electrostimulation electrodes. The system can help reduce the chance for user error or incorrect maintenance of electrodes. In an example, the neurostimulation therapy system can include or use an electrostimulation electronics unit capable of delivering electrostimulation to a subject via two or more skin electrodes. The neurostimulation therapy system can include battery charging circuitry configured to charge a battery of the electrostimulation electronics unit through the skin electrodes. The skin electrodes can include a hydrophilic polymer layer, and the battery charging circuitry can be configured to pass charge across the hydrophilic polymer layer and to the battery of the electrostimulation electronics unit. In an example, the two or more skin electrodes each respectively include capacitive coupling (e.g., coupled using series DC-blocking capacitors, e.g., in a charge-balanced arrangement) between corresponding two or more output terminals of the electrostimulation electronics unit, and the battery charging circuitry can be configured to be capacitively coupled via the two or more output terminals to the electrostimulation electronics unit for battery charging. In several systems and methods described herein, the battery charging circuitry can be a component of a docking station for storing the electrostimulation electronics unit absent use for electrostimulation.

Figure 1B:
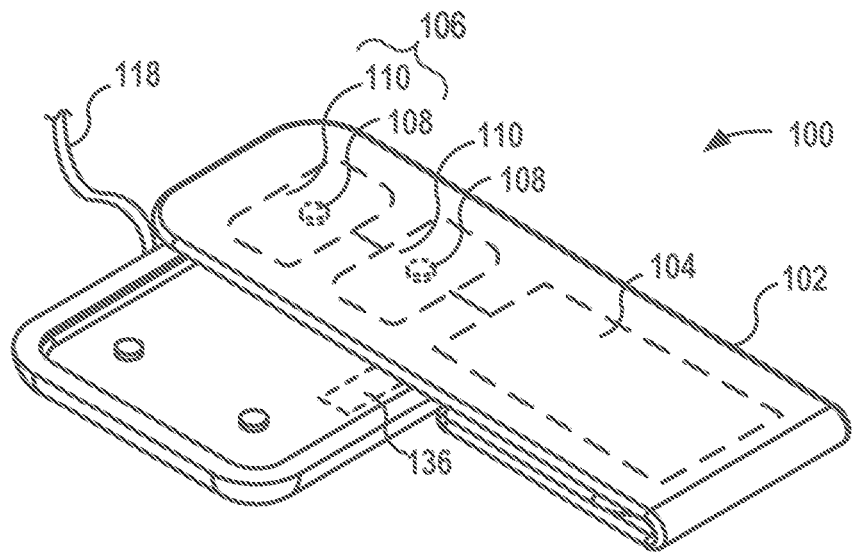
FIG. 1B depicts a perspective view of a transcutaneous neurostimulation therapy system.

FIG. 1A and FIG. 1B depict a perspective view of an example of a transcutaneous neurostimulation therapy system 100. In an example, the electrostimulation therapy system 100 can include a wearable electrostimulation device 102, an electrostimulation electronics unit 104, two or more electrodes 106, a device docking station 112, two or more battery charging contacts 150, battery charging circuitry 136, and a power supply line 118. The electrostimulation therapy system 100 can function to deliver neurostimulation therapy to skin of a subject via the electrodes 106, and the system can help enable convenient electrode storage while concurrently charging a battery of the electrostimulation electronics unit 104 while the wearable electrostimulation device 102 is not in use for electrostimulation.

The wearable electrostimulation device 102 can be worn by the subject and can include or use the electrostimulation electronics unit 104 coupled to the electrodes 106, such as for transcutaneously delivering a neurostimulation signal. Herein, the term neurostimulation can generally refer to types of therapy also known elsewhere as transcutaneous electrical nerve stimulation (TENS), electrical muscle stimulation (EMS), electrical stimulation (e-stim), or electrical neurostimulation. The wearable electrostimulation device 102 can be sized and shaped to be able to be attached or held to a body location of the subject, e.g., a leg, arm, foot, waist, neck, head, or chest of the subject. In an example depicted by FIG. 1A and FIG. 1B, the wearable electrostimulation device 102 can include or use a strap to help hold the electrodes 106 to the skin of the subject. While electrodes are generally described herein with a focus on providing electrostimulation to a subject, the electrodes can alternatively or additionally be used such as to help detect or measure one or more biosignals or biopotentials from the subject. A particular electrode 106 can include or use an electrode terminal 108 and an electrode pad 110. For example, the electrode terminal 108 can receive a capacitively-coupled (e.g., coupled using series DC-blocking capacitors, e.g., in a charge-balanced arrangement) electrostimulation signal from the electrostimulation electronics unit 104, and can deliver a resulting neurostimulation signal to the skin of the subject, such as via the electrode pad 110. In an example, multiple electrodes, such as two electrodes 106, can be used. For a bipolar electrode example having two electrodes 106, this can a first electrode 106A that can serve as an anode and a second electrode 106B, such as which can serve as a cathode. Also, a plurality of electrodes 106 can be arranged to form a multi-electrode group, matrix, or array such as for one or both of sensing or for delivering the electrostimulation signal to the skin of the subject. In an example, each electrode terminal 108 can be an electrode contact fixed to the wearable electrostimulation device 102 and each corresponding electrode pad 110 can be removably coupled to the device 102. In other examples, the electrode pad can be fixed to the wearable electrostimulation device 102. Because the current density of the neurostimulation signal at the electrode terminal 108 may be larger than desired, the electrode pad 110 may include an embedded or other arrangement of electrical conductors that can help distribute the electrostimulation signal current over a larger effective surface area for delivery to the subject at the skin-electrode interface. The electrode pad can be formed of a hydrogel, a hydrophilic polymer such as polyvinyl alcohol (PVA), carbon, textiles, or other types of conductive or dielectric gels, polymers, or textiles.

The electrode terminal 108 can supply an alternating current (AC) electrostimulation signal for delivery to the skin by the electrode 106. The electrostimulation signal can be supplied by the electrode terminal 108 at a frequency between about 4 kHz to about 15 kHz such as for treating Restless Leg Syndrome (RLS) or Periodic Limb Movement Disorder (PLMD), such as described in Charlesworth U.S. Pat. No. 11,103,691, which is hereby incorporated by reference herein. The wearable electrostimulation device 102 can include or use capacitive coupling such as to provide a higher resistance to direct current (DC) signal before reaching the electrode terminal 108 while providing a lower resistance to AC signal. In an example, the capacitive coupling includes one or more capacitors (also referred to decoupling capacitors) included in series between each electrode terminal 108 and the electrostimulation electronics unit 104. The one or more capacitors can also be included in series between each electrode terminal 108 and the battery of the electrostimulation electronics unit 104. The electrostimulation signal can be delivered from the electrode terminal 108 to the skin through the electrode pad 110 disposed therebetween.

The electrostimulation electronics unit 104 can include or use or be coupled to a rechargeable battery. While generally described herein as a battery, other types of energy stores can be used such as supercapacitors. Generation of the electrostimulation signal can at least partially deplete the battery of charge, and the electrostimulation electronics unit 104 can be coupled to the battery charging circuitry 136 through, e.g., the battery charging contacts 150. In an example depicted in FIG. 1A and FIG. 1B, the electrostimulation electronics unit 104 can be coupled through the electrodes 106 and through the battery charging contacts 150 to the battery charging circuitry 136. The battery charging circuitry 136 can supply a charging signal delivered through the battery charging contacts 150, and the charging signal can be an alternating current (AC) signal. The charging signal can be supplied at a different frequency than that of the electrostimulation signal. In an example, the charging signal can be supplied by battery charging contacts 150 at a frequency between about 1 kHz to about 100 kHz. In another example, the charging signal can be supplied by the battery charging contacts 150 at a similar frequency to that of the electrostimulation signal. Systems included herein can use a battery charging circuitry generating a charging signal such as to charge a battery without supplying inductive charging to the battery, an electrostimulation electronics unit, or a wearable electrostimulation device.

The battery charging circuitry can generate the charging signal which can be capable of traversing or passing through the electrode pad 110 while maintaining sufficient voltage for charging the battery. For instance, the battery charging circuitry 136 can generate the charge signal such as to pass electric current across a hydrophilic polymer layer of the electrode pad 110. In an example, the electrode pad 110 can have an impedance greater than about 100 ohms (Ω). In another example, the electrode pad 110 can have an impedance greater than about 300 ohms (Ω).

The electrode pad 110 can have a large enough impedance such as to require the charging signal to be supplied at a voltage of greater than 10V such as to maintain sufficient voltage for charging the battery after traversing the electrode pad 110. In an example, the charging signal can be supplied by the battery charging contacts 150 at a voltage between about 10V and about 42V. In an example, the charging signal can be supplied by the battery charging contacts 150 at a voltage between about 20V and about 42V. The charging signal can be supplied by the battery charging contacts 150 at a voltage between about 20V and about 35V The charging signal can be supplied by the battery charging contacts 150 at a voltage greater than 42V.

The charging signal can be supplied in a sinusoidal waveform, or alternatively in a non-sinusoidal waveform such as a square waveform. In an example, the charging signal can be supplied in a charge-balanced waveform. In an example, the battery charging circuitry 136 can include or use a charge-balancing circuit such as to ensure there is not an excessive DC offset between a charging waveform generator of the battery charging circuitry 136 and the electrodes 106. Here, the system 100 can include or use a DC offset measuring circuit at the electrodes 106.

The DC offset measuring circuit can be communicatively coupled with the charge-balancing circuit of the battery charging circuitry 136, and the battery charging circuitry 136 can utilize a measurement of DC offset at the electrodes 106 such as to alter a duty cycle at the charging waveform generator such as to restore charge-balance.

In an example, the wearable electrostimulation device 102 can be sized and shaped such as to be interfaced with or be received within a receptacle of a device docking station 112. As depicted in FIG. 1A and FIG. 1B, the wearable electrostimulation device 102 can be placed with the electrodes 106 facing the docking station 112 such as to electrically connect the electrodes 106 to the battery charging contacts 150. In some examples, each battery charging contact 150 can correspond with one single electrode 106. Here, the electrodes 106 and corresponding battery charging contacts 150 can be sized, shaped, and spaced relative to one another such that an electrical connection is made between each corresponding pair without shorting (electrical connections outside of corresponding pairs). As depicted in FIG. 1B, at least a portion of the wearable electrostimulation device 102 can be folded, rolled, or otherwise compacted such as to minimize the space required for device docking. In another example, the electrode pads 110 can be removed from the wearable electrostimulation device 102, and the wearable electrostimulation device 102 can be placed with the electrodes 106 facing the docking station 112 such as to electrically connect the electrodes terminals 108 directly to the battery charging contacts 150. In some examples, as depicted in FIG. 1A and FIG. 1B, the docking station 112 can be sized and shaped such as to be capable of receiving more than one (e.g., a pair of) wearable electrostimulation devices 102 for e.g., battery charging. Here, the docking station can be capable of concurrent battery charging of more than one battery in examples similar to those described herein with respect to charging of a single battery. In an example, two or more wearable electrostimulation devices 102 connecting to a single docking station can be charged by the battery charging circuitry 136.

The docking station 112 or the battery charging circuitry 136 can be capable of withstanding the electrostimulation signal from the electrode pads 110. The battery charging circuitry 136 can sustain electrical contact with the electrostimulation signal without significant damage to the battery charging circuitry. For instance, the charging waveform generator of the battery charging circuitry 136 can be capable of withstanding an electrostimulation signal including bidirectional current without significant damage to the charging waveform generator. Also, the battery charging circuitry 136 can include or use a diode steering circuit, and the diode steering circuit can direct the electrostimulation signal to an electrostimulation detection circuit within the battery charging circuitry 136 for absorption of current and detection of electrostimulation output during battery charging or device docking. Alternatively or additionally, the battery charging circuitry 136 can include a device detection circuit. The device detection circuit can detect the presence of the electrode pads 110 being coupled with the battery charging contacts 550. For example, the battery charging circuitry 136 can idle while generating a test pulse signal. An impedance of the test pulse signal can be detected by the device detection circuit when electrode pads 110 are present. The battery charging circuitry 136 can alternate or switch from generating the test pulse signal and generating the charging signal based on the presence of the electrode pads 110 detected by the device detection circuit.

In examples described in further detail below, the electrostimulation electronics unit 104 can communicate with the battery charging circuitry 136 such as to coordinate operating modes of the neurostimulation therapy system 100 between system components. In one example, the communication can be a wireless communication between system components. Also, the electrostimulation electronics unit 104 can communicate with the battery charging circuitry 136 via a wired connection, and the wired connection can be the coupling between electrostimulation electronics unit 104 through the electrodes 106 and through the battery charging contacts 150 to the battery charging circuitry 136. Here, the electrostimulation electronics unit 104 can communicate with the battery charging circuitry 136 via the battery charging connection while the battery is charging. The electrostimulation electronics unit 104 can also communicate with the battery charging circuitry 136 via the battery charging connection while the battery is not charging. Communication between the electrostimulation electronics unit 104 and the battery charging circuitry 136 can include instructions to impede supply of the electrostimulation signal, instructions to impede supply of the charging signal, or both.

In an example, the system 100 can also include an electrode rehydrator, which can help rehydrate the electrode pad, such as based on an indicator, a water content of the electrode pad, or an impedance of the electrode pad. The electrode rehydrator can be a component of the docking station for storing the electrostimulation electronics unit absent use for electrostimulation and the electrode rehydrator can rehydrate the electrode pad concurrent with battery charging from battery charging circuitry, such as described in Jeffrey U.S. Provisional Patent Application Ser. No. 63/270,022 entitled REHYDRATABLE ELECTRODE FOR NEUROSTIMULATION, filed on even date herewith, which is incorporated by reference herein in its entirety.

FIG. 2A and FIG. 2B show a depiction of an example wearable electrostimulation device in use on a subject. In an example, an electrostimulation therapy system 100 can include a wearable electrostimulation device 102, an electrostimulation electronics unit 104, and one or more electrodes 106. The electrostimulation therapy device 102 can function to deliver neurostimulation therapy to skin of a subject via the electrodes 106, and the device can be capable of delivering such therapy over multiple therapy sessions. As depicted in FIG. 2A & FIG. 2B, the wearable electrostimulation device 102 can include or use a strap, sleeve, band, or clamp to help hold the electrodes 106 to the skin of the subject. In another example, the electrostimulation device can include or use an adhesive or can connect to other items wearable by the subject, e.g., hats, clothing, etc. Alternatively, the wearable electrostimulation device 102 can be sufficiently wearable on the skin surface of the patient by adhesion forces of the electrodes 106 alone without the need for additional features to help hold the device 102 to the subject. The wearable electrostimulation device 102 can be attached or held to a body location of the subject, e.g., a leg, arm, foot, waist, neck, head, or chest of the subject at or near a nerve location of the patient skin for transcutaneous neurostimulation thereof. The wearable electrostimulation device 102 can include or use the electrostimulation electronics unit 104 for producing an electrostimulation signal which can be distributed to the skin surface of the subject by the electrodes 106. The electrostimulation signal delivered to the skin surface of the subject by the electrodes 106 can be alternating current (AC) signal, and the AC signal can be significantly charge-balanced. In an example, the electrostimulation electronics unit 104 can include capacitive-coupling circuitry such as capacitors in series for distributing AC signal to the skin surface of the subject without distributing significant amounts of direct current (DC) signal to the skin surface of the subject. In an example, the wearable electrostimulation device 102 can be e.g., fastened to a body location of the subject for a transdermal neurostimulation therapy session. The electrostimulation therapy session can be performed for a predetermined period of time. The electrostimulation therapy session can be a recurrent therapy session, such as can be included as a member within a larger schedule of electrostimulation therapy sessions. In an example, the electrostimulation therapy session can be repeatable. In examples where multiple electrostimulation therapy sessions can be performed, the wearable electrostimulation device 102 can be placed or stored at a docking station (as depicted in FIG. 1B) between some of the therapy sessions such as to charge a battery of the electrostimulation electronics unit 104.

Figure 3:
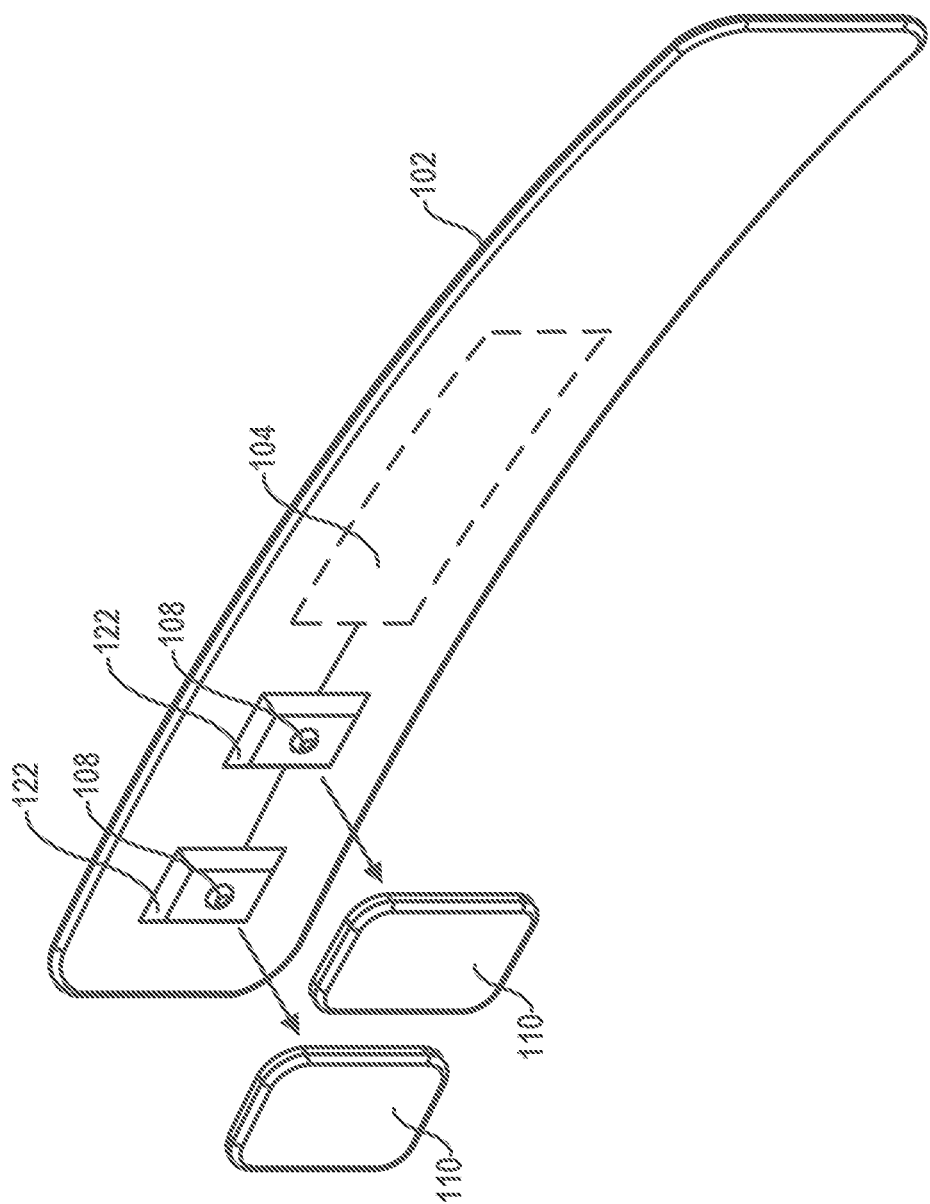
FIG. 3 depicts a perspective view of an example of skin electrode pads being used with an electrostimulation electronics unit.

FIG. 3 depicts a perspective view of an example of skin electrode pads being used with an electrostimulation electronics unit of a wearable electrostimulation device. In an example, an electrostimulation therapy system 100 can include a wearable electrostimulation device 102, an electrostimulation electronics unit 104, and one or more electrodes 106. The wearable electrostimulation therapy device 102 can function to deliver neurostimulation therapy to skin of a subject via the electrode pads 110 which help make up the electrodes 106 (as depicted in FIG. 1A). In an example, the electrode pads 110 can be removably coupled to the wearable electrostimulation device 102. The electrode pads 110 can each be attached to a pairing surface 122 of the wearable electrostimulation device 102. The pairing surface 122 can include the electrode terminal 108 e.g., disposed therein, and the electrode terminal 108 can be electrically connected to the electrostimulation electronics unit 104. In an example, as depicted in FIG. 3, two or more electrode pads 110 are each paired to corresponding pairing surfaces 122 including one electrode terminals 108. In another example, one electrode pad 110 can be paired to an electrode pairing surface 122 containing more than one electrode terminal 108, or one electrode pad can span multiple electrode pairing surfaces 122 containing one or more electrode terminals 108. The electrode pad 110 can be removed for, e.g., hygienic maintenance, electrode maintenance such as rehydrating, or disposal. As discussed further herein, the electrode pads can be removed based upon, e.g., detection of an electrode pad condition by the electrostimulation electronics unit 104.

Figure 4:
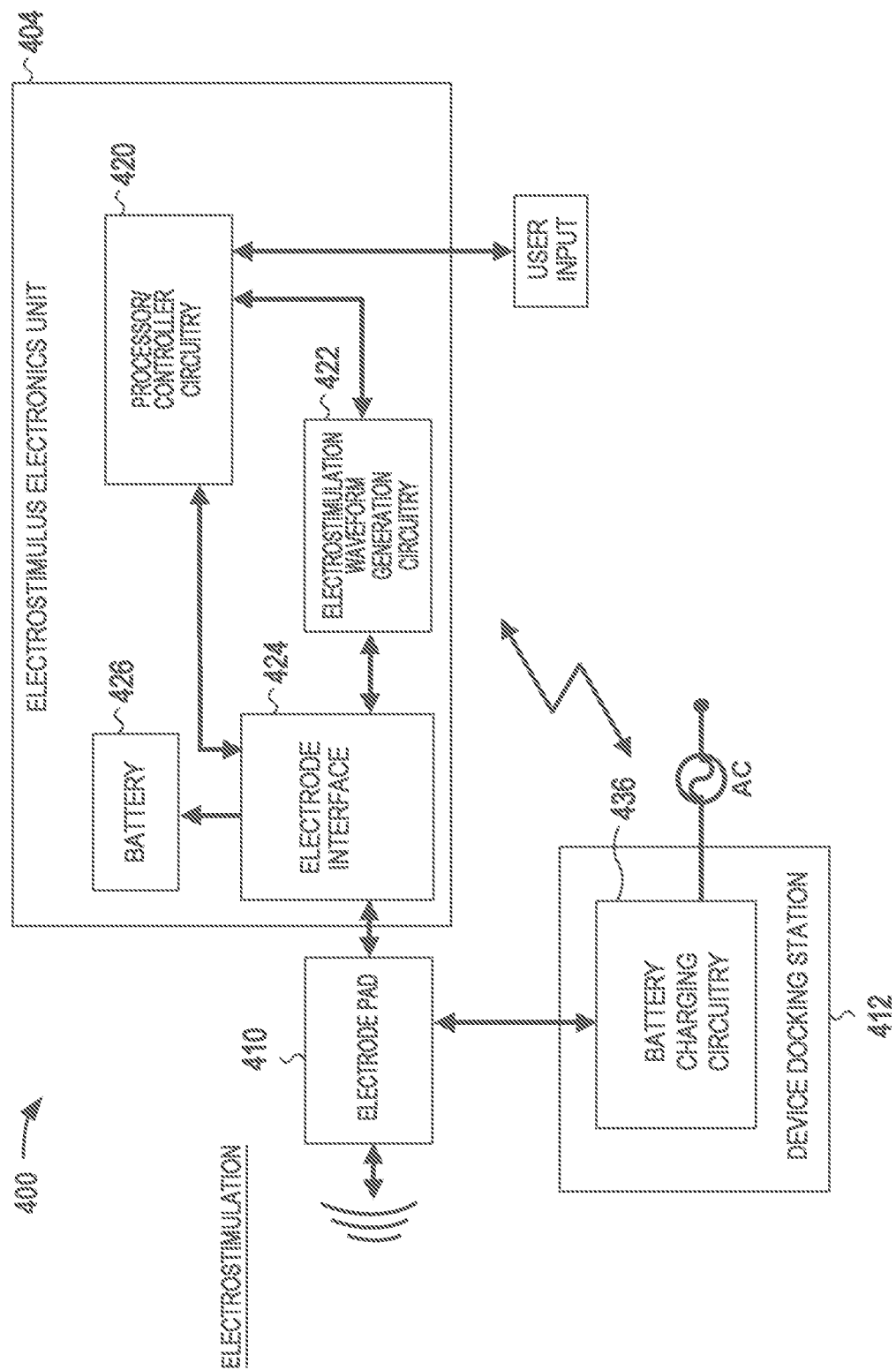
FIG. 4 is a schematic representation of an example of a transcutaneous neurostimulation therapy system.

FIG. 4 is a schematic representation of an example of a transcutaneous neurostimulation therapy system. An example electrostimulation therapy system 400 can include an electrostimulation electronics unit 404, one or more electrode pads 410, a docking station 412 and a battery charging circuitry 436. The electrostimulation therapy system 400 can be similar in many respects to electrostimulation therapy system 100. The components, structures, configuration, functions, etc. of system 400 can therefore be the same as or substantially similar to that described in detail above with reference to system 100. The electrostimulation therapy system 400 can include the electrostimulation electronics unit 404 capable of communication with either of the docking station 412 or the battery charging circuitry. The electrostimulation electronics unit 404 can include or use a processor or controller circuitry 420, an electrostimulation waveform generator circuitry 422, an electrode interface 424, and a battery 426. The processor circuitry can receive a user input such as communications from a user interface (UI). The UI can include or use switches, buttons, knobs, touch panels, status LEDs, or display screens such as to enable user interaction for performing electrostimulation therapy. The display, status LEDs, or other similar components can be capable of displaying or indicating user data, test outcomes, or instructions. In one example the display can be an LCD screen embedded in either of the wearable electrostimulation device of the electrostimulation electronics unit 404. Alternatively or additionally, the user can interact with the electrostimulation electronics unit 404 by means of the software application on a remote device such as a computer or a mobile phone.

The processor circuitry 420 can be communicatively coupled with the electrostimulation waveform generator circuitry 422. The electrostimulation waveform generator circuitry 422 can be selectively operated by the processor circuitry 420 such as to provide an electrostimulation signal to the electrode interface 424. The electrostimulation signal can be generated by the generator circuitry 422 at a frequency within a range of about 4 kHz to about 15 kHz and the waveform can be sinusoidal. The electrode interface 424 can supply the electrostimulation signal to the electrode pads 410 via electrostimulation output terminals. In an example, the electrode interface 424 can be communicatively coupled to the processor circuitry 420 such as to provide feedback or instructions.

The battery charging circuitry 436 can be at least partially disposed within a docking station 412. The battery charging circuitry 436 can be connected to an energy source, and the battery charging circuitry 436 can supply a charging signal to the battery 426 through one or more electrode pads. For instance, the electrode interface 424 can include or use circuitry for controlling distribution of the charging signal to the battery 426. The battery charging circuitry 436 can be capable of communication with the electrostimulation electronics unit 404 such as to help moderate battery charging from the battery charging circuitry 436 or output of the electrostimulation signal from the electrode interface 424. In an example, the battery charging circuitry 436 can be in wireless communication with the electrostimulation electronics unit 404 such as to communicate instructions between. e.g., the battery charging circuitry 436 and the processor circuitry 420. Communications between the battery charging circuitry 436 and the electrostimulation electronics unit 404 are described in greater detail below.

Figure 5:
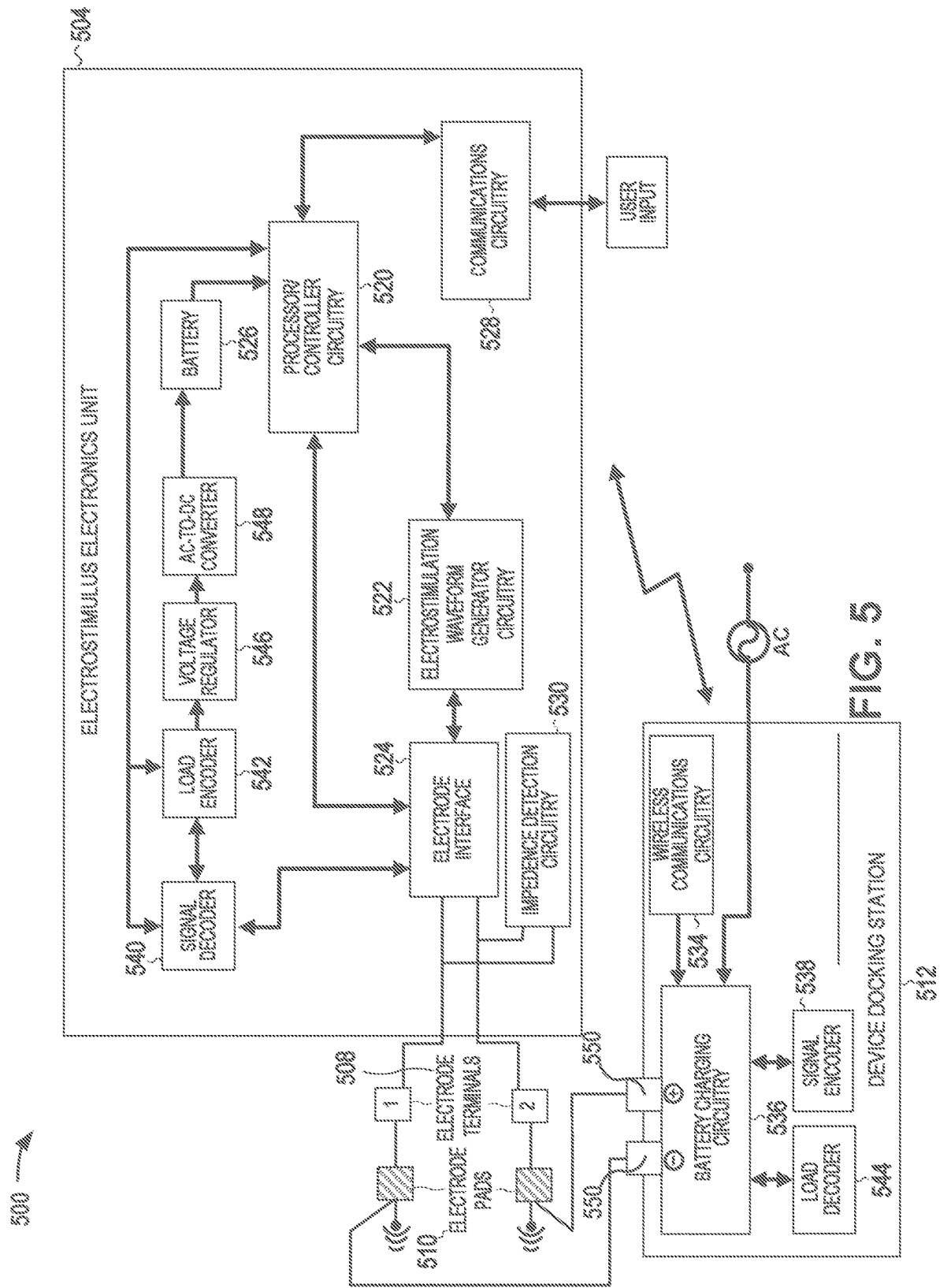
FIG. 5 is a schematic representation of an example of a transcutaneous neurostimulation therapy system.

FIG. 5 is a schematic representation of an example of a transcutaneous neurostimulation therapy system. An example electrostimulation therapy system 500 can include an electrostimulation electronics unit 504, electrode terminals 108, electrode pads 510, a docking station 512 and battery charging circuitry 536. The electrostimulation therapy system 500 can be similar in many respects to electrostimulation therapy systems 100 and 400. The components, structures, configuration, functions, etc. of system 500 can therefore be the same as or substantially similar to that described in detail above with reference to systems 100 and 400. Similar to that previously described with respect to system 400, system 500 can include the electrostimulation electronics unit 504 capable of communication with either of the docking station 512 or the battery charging circuitry 536. The electrostimulation electronics unit 504 can include or use a processor or controller circuitry 520, an electrostimulation waveform generator circuitry 522, an electrode interface 524, and a battery 526. The electrostimulation electronics unit 504 can also include communications circuitry 528, impedance detection circuitry 530, a signal decoder 540, a load encoder 542, a voltage regulator 546, or an AC-to-DC converter 548. Also, the battery charging circuitry 536 can include or use or be coupled to a signal encoder 538, a load decoder 544, or wireless communications circuitry 534. The system 500 can also include or use a system controller communicatively coupled to one or more system components.

The charging signal supplied by the battery charging circuitry can be a symmetrical AC waveform. The charging signal can be delivered to the electrostimulation electronics unit 504 through the electrode pads 510, and the charging signal can be selectively distributed by the electrode interface 524 to a voltage regulator 546. The voltage regulator can be electrically coupled between the electrode terminals 508 and the battery 526. The voltage regulator 546 can regulate the voltage of the charging signal to a suitable voltage for charging the battery 526. The voltage regulator 546 can regulate the voltage of the charging signal to be relatively close to the voltage of the battery. For instance, the voltage regulator 546 can regulate the voltage of the charging signal to be within a range between about 3V to about 5V. The voltage regulator 546 can regulate the voltage of the charging signal to be about 4.2V Also, the voltage regulator 546 can regulate the voltage of the charging signal to near a predetermined intermediate voltage between the voltage of the charging signal supplied by the battery charging circuitry 536 and a suitable voltage for charging the battery 526. For instance, the voltage regulator 546 can regulate the voltage of the charging signal to be within a range of about 4.4V to about 10V. The voltage regulator 546 can regulate the voltage of the charging signal to be about 4.5V. The voltage regulator can also stabilize the voltage of the charging signal such as to minimize voltage fluctuation prior to delivery to the battery 526 for charging. The voltage regulator 546 can pass the voltage-regulated, AC charging signal to the AC-to-DC converter 548, and the AC-to-DC converter 548 can convert the AC waveform to a DC waveform for charging the battery 526. The AC-to-DC converter 548 can include or use a rectifier, power supply unit (PSU), switched-mode power supply, or combinations thereof. The battery 526 can be any type of rechargeable battery such as Lithium-ion battery (Li-ion), nickel-cadmium (NiCd), nickel-metal hydride (NiMH), or Lithium-ion polymer (LiPo). The battery 526 can include or use one or more DC components for applying direct current.

Any of the battery charging circuitry 536, signal encoder 538, a load decoder 544, or wireless communications circuitry 534 can be at least partially disposed or contained within the docking station 512. The wireless communications circuitry 534 can communicate wirelessly with communications circuitry 528 of the electrostimulation electronics unit 504 such as to exchange instructions between the two. In an example, the communications circuitry 528 can also be wirelessly or electrically coupled to a user interface (UI) such as an onboard UI or software for providing user input from a remote device. Wireless communication can be a BLUETOOTH connection, a Wi-Fi connection, a cellular connection, a near-field communication (NFC) connection, a radiofrequency (RF) connection, or combinations thereof. In an example, the wireless communications circuitry 534 or the communications circuitry 528 can include or use a BLUETOOTH chip capable of broadcasting e.g., in the 2.4 GHz industrial, scientific, and medical (ISM) radio band. In another example, wireless communications circuitry 534 can communicate with the communications circuitry 528 or the processor circuitry 520 through a wired connection, such as a USB connection. In another example, battery charging circuitry 536 can communicate with the communications circuitry 528 or the processor circuitry 520 through the one or more electrode pads, such as through neurostimulation output terminals. Here, the battery charging circuitry can be capable of generating a communications signal to be received by the electrostimulation electronics unit 504. Also, the battery charging circuitry 536 can encode data onto the charging signal to be received by the electrostimulation electronics unit 504. For instance, the signal encoder 538 can be included in or used by the battery charging circuitry 536 such as to encode data onto the waveform of the charging signal. The waveform of the charging signal can be modulated by the signal encoder 538, such as through amplitude modulation (AM), frequency modulation (FM), or pulse-width modulation (PWM). The electrostimulation electronics unit 504 can include or use the signal decoder 540 such as for decoding data encoded onto the charging signal waveform. The signal decoder 540 can be communicatively coupled with the processor circuitry 520 such as for transmitting communications thereto. The electrostimulation electronics unit can also encode data onto the charging signal to be received by the battery charging circuitry 536. For example, the electrostimulation electronics unit 504 can include or use or be coupled to the load encoder 542, and the load encoder 542 can modulate data into the charging signal such as by changing or interrupting the load current. For instance, the load encoder 542 can briefly interrupt charging of the battery or briefly draw extra load such as to modulate data into the charging signal. Also, the battery charging circuitry 536 can include or use or be coupled to the load decoder 544 such as for decoding data encoded onto the charging signal waveform. For example, the load decoder 544 can include or use a current measurement circuit for detecting modulation of the current such as by the load encoder 542.

The communications between the electrostimulation electronics unit 504 and the battery charging circuitry 536 can include instructions which can be read by either of the processor circuitry 520 or the battery charging circuitry 536 to control operations of the electrostimulation output of the electrostimulation electronics unit 504 or a battery charging output of the battery charging circuitry 536, respectively. In an example, either of the communications circuitry 528 or the wireless communications circuitry 534 can be capable of determining the proximity of the battery charging circuitry 536 and the electrostimulation electronics unit 504. Where the two have at most a predetermined proximity to each other, the communications circuitry 528 or the wireless communications circuitry 534 can deliver instructions for either of the electrostimulation electronics unit 504 or the battery charging circuitry 536 to enter a charging mode. In the charging mode, the battery charging circuitry 536 can be selectively operated by, e.g., the battery charging circuitry 536 such as to supply charge at the battery charging contacts 550. Also, in the charging mode, either of the electrostimulation waveform generator circuitry 522 or the electrode interface 524 can be selectively operated by the processor circuitry 520 such as to cease electrostimulation output distributed by the one or more electrode pads 510 during charging.

In another example, the communications between the electrostimulation electronics unit 504 and the battery charging circuitry 536 can include instructions which can be read by either of the processor circuitry 520 or the battery charging circuitry 536 such as to impede one or more system functions until a compliant electrode pad 510 is supplied or replaced in connection with the electrostimulation electronics unit 504. For example, the processor 520 can impede electrostimulation output until receiving communications or detecting that a compliant electrode pad 510 has been supplied or replaced. Also, the battery charging circuitry 536 can impede battery charging until receiving communications or detecting that a compliant electrode pad 510 has been supplied or replaced. Likewise, the battery charging circuitry 536 can impede battery charging until receiving communications or detecting that a compliant electrode pad 510 has been supplied or replaced. Compliance of the one or more electrode pads 510 can be detected by a circuit located in any of the electrostimulation electronics unit 504, the battery charging circuitry 536, or the docking station 512. In an example, the electrode pad 510 can include or use a usability indicator including an initiator such as an NFC chip attached to or embedded within the pad 510 for communication with, e.g., the communications circuitry 528 or the wireless communications circuitry 534. The usability indicator can transmit, e.g., a radiofrequency signal to be read by an indicator reader included in circuitry 528 or 534. Circuitries 528 or 534 can include or use memory including instructions to impede one or more system functions upon detection (or instructions of) an electrode pad without a compliant usability indicator or an electrode pad that has exceeded a predetermined amount of uses in electrostimulation. In another example, the electrostimulation electronics unit 504 can include or use impedance detection circuitry 530 which can be capable of measuring an impedance or resistance across the one or more electrode pads 510. The impedance detection circuitry 530 can be communicatively coupled to the processor circuitry 520. In an example, circuitries 528 or 534 can include or use memory including instructions to impede one or more system functions upon detection (or instructions of) an electrode pad 510 having an impedance deviating from the expected operating conditions and which is indicative of deteriorated electrode pad electrical performance. In an example, the impedance detection circuitry 530 provides a classifier signal indicative of electrode pad impedance exceeding 10% deterioration from a new-electrode-pad impedance. Impedance of the electrode pad 510 measured by the impedance detection circuitry 530 can also be detected by or communicated to the battery charging circuitry 536 such as to influence generation of the charging signal by the battery charging circuitry 536. In an example, the battery charging circuitry 536 can include or use memory including instructions to impede battery charging upon detection (or instructions of) an electrode pad 510 having an impedance deviating from the expected operating conditions and which is indicative of deteriorated electrode pad electrical performance, such as exceeding 10% deterioration from a new-electrode-pad impedance. In an example, the impedance of the electrode pad 510 can be recurrently, periodically, or continually monitored by the impedance detection circuitry 530. The battery charging circuitry 536, the docking station 512, or the electrostimulation electronics unit 504 can also include other components capable of measuring or estimating moisture content or saturation measuring of the electrode pad 510 such as to help the system 500 determine the condition of the electrode pads 510 before battery charging for use in electrostimulation therapy. Alternative or additional components for measuring or estimating moisture content or saturation can include moisture meters or hygrometers.

The electrostimulation therapy system can include or use a system controller, and the system controller can be located within or be connected to the processor/controller circuitry or the battery charging circuitry, or the system controller can be remotely located. System controller can include hardware, software, and combinations thereof to implement the functions attributed to the controller herein. System controller can be an analog, digital, or combination analog and digital controller including a number of components. As examples, controller can include ICB(s), PCB(s), processor(s), data storage devices, switches, relays, etcetera. Examples of processors can include any one or more of a microprocessor, a controller, a digital signal processor (DSP), an application specific integrated circuit (ASIC), a field-programmable gate array (FPGA), or equivalent discrete or integrated logic circuitry. Storage devices, in some examples, are described as a computer-readable storage medium. In some examples, storage devices include a temporary memory, meaning that a primary purpose of one or more storage devices is not long-term storage. Storage devices are, in some examples, described as a volatile memory, meaning that storage devices do not maintain stored contents when the computer is turned off Examples of volatile memories include random access memories (RAM), dynamic random-access memories (DRAM), static random-access memories (SRAM), and other forms of volatile memories known in the art. The data storage devices can be used to store program instructions for execution by processor(s) of controller. The storage devices, for example, are used by software, applications, algorithms, as examples, running on and/or executed by controller. The storage devices can include short-term and/or long-term memory and can be volatile and/or non-volatile. Examples of non-volatile storage elements include magnetic hard discs, optical discs, floppy discs, flash memories, or forms of electrically programmable memories (EPROM) or electrically erasable and programmable (EEPROM) memories.

System controller can be configured to communicate with the electrostimulation therapy system 500 and components thereof via various wired or wireless communications technologies and components using various public and/or proprietary standards and/or protocols. For example, a power and/or communications network of some kind may be employed to facilitate communication and control between controller and electrostimulation therapy system 500. In one example, system controller can communicate with electrostimulation therapy system 500 via a private or public local area network (LAN), which can include wired and/or wireless elements functioning in accordance with one or more standards and/or via one or more transport mediums. In one example, controller and electrostimulation therapy system 500 can be configured to use wireless communications according to one of the 802.11 or Bluetooth specification sets, or another standard or proprietary wireless communication protocol. Data transmitted to and from components of electrostimulation therapy system 500, including controller, can be formatted in accordance with a variety of different communications protocols. For example, all or a portion of the communications can be via a packet-based, Internet Protocol (IP) network that communicates data in Transmission Control Protocol/Internet Protocol (TCP/IP) packets, over, for example, Category 5, Ethernet cables.

System controller can selectively operate several components in example electrostimulation systems included herein. System controller can include one or more programs, circuits, algorithms, or other mechanisms for controlling the operation of electrostimulation therapy system 500. For example, the system controller can be configured to selectively operate charging waveform generator circuitry, electrostimulation waveform generator circuitry, signal modulators, or other components of electrostimulation therapy systems described herein.

FIG. 6A and FIG. 6B are flowcharts showing operation of an examples of transcutaneous neurostimulation systems 600A and 600B, respectively. Transcutaneous neurostimulation systems described herein can utilize communications between an electrostimulation electronics unit and battery charging circuitry such as to coordinate operations between the two. Transcutaneous neurostimulation systems can also utilize independent detection capabilities of the electrostimulation electronics unit and the battery charging circuitry, respectively, without communications between the two such as to coordinate similar operations. At 602, the electrostimulation electronics unit can be coupled to the battery charging circuitry such as by electrically coupling the electrodes with corresponding battery charging contacts. Coupling of the electrostimulation electronics unit with the battery charging circuitry can involve interfacing or placing the electrostimulation electronics unit within a receptacle of a device docking station. At 604, upon electrical coupling, at least one of the electrostimulation electronics unit or the battery charging circuitry can detect for the presence of an electrostimulation signal at the electrodes. At 606, if the electrostimulation signal is detected at the electrodes, a charging signal can be inhibited from the battery charging contacts, and the battery of the electrostimulation electronics unit will not be charged. Also, before or after the charging signal is inhibited to the battery charging contacts, the electrostimulation signal can be inhibited to the electrodes. Alternatively or additionally, the electrostimulation signal can be inhibited to the electrodes based on the detection of the electrostimulation signal at the electrodes and regardless of whether the charging signal is inhibited to the battery charging contacts. At 608, if no electrostimulation signal is detected at the electrodes, the charging signal can be supplied at the charging contacts to the electrodes for battery charging.

Also, at 612, at least one of the electrostimulation electronics unit or the battery charging circuitry can detect for presence of the charging signal at the electrodes or can detect for a certain predetermined proximity of the electrostimulation electronics unit to the battery charging circuitry. At 614, if the two are proximate, or if the charging signal is detected at the electrodes, the electrostimulation signal can be inhibited to the electrodes or the charging signal can be inhibited to the battery charging contacts. At 616, if no charging signal is detected at the electrodes or no proximity between the electrostimulation electronics unit and the battery charging circuitry is detected, the transcutaneous neurostimulation system 600B can proceed to follow other system instructions without interruption. If no charging signal is detected at the electrodes, the transcutaneous neurostimulation system 600B can also wait and listen for subsequent detection of the charging signal at electrodes or for proximity of the electrostimulation electronics unit to the battery charging circuitry.

Figure 7:
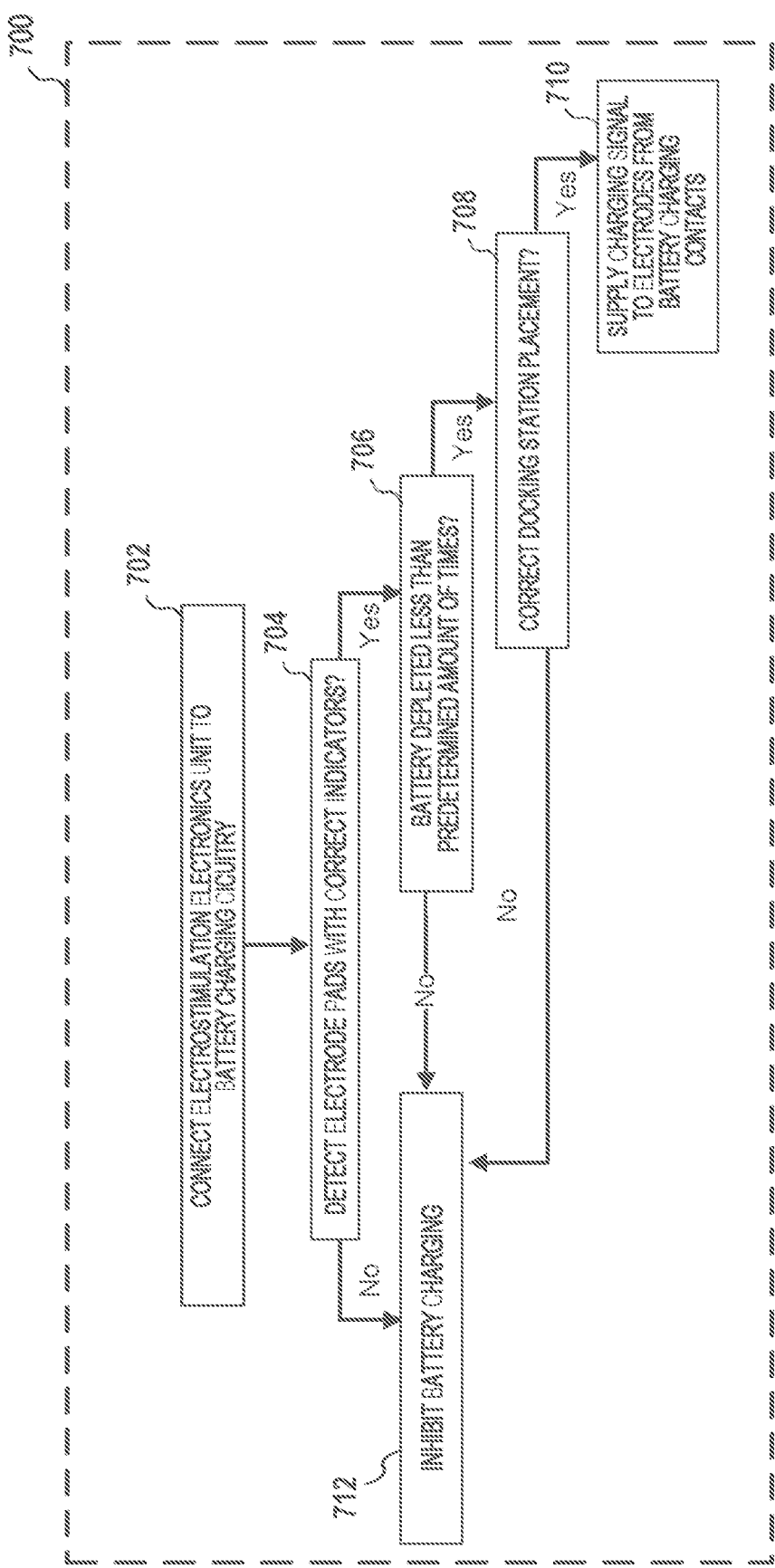
FIG. 7 is a flowchart of an example of a transcutaneous neurostimulation therapy system.

FIG. 7 is a flowchart showing operation of an example of a transcutaneous neurostimulation system 700. At 702, the electrostimulation electronics unit can be coupled to the battery charging circuitry such as by electrically coupling the electrodes with corresponding battery charging contacts. Coupling of the electrostimulation electronics unit with the battery charging circuitry can involve interfacing or placing the electrostimulation electronics unit within a receptacle of a device docking station. At 704, either of an electrostimulation electronics unit or a battery charging circuitry can detect for the presence of compliant electrode pads such as for a prerequisite to certain system operations. At 706, if the electrode pads contain the correct usability indicators, the transcutaneous neurostimulation system 700 can determine the number of uses of the electrode pads based on a counting circuit of the system. For instance, the counting circuit can count the amount of battery depletions that occur with an electrode pad carrying the same usability indicator. At 708, if the battery has been depleted less than the predetermined acceptable number of times, the transcutaneous neurostimulation system 700 can determine whether the electrostimulation electronics unit has been paired to the correct terminals or in the correct orientation at the docking station. For instance, where two or more electrostimulation electronics units can pair with a single dock, each electrostimulation electronics unit can have a designated location on the dock or designated corresponding battery charging contacts. At 710, if all above conditions are met, the charging signal can be supplied to the electrodes from the battery charging contacts. At 712, if any of the above conditions are not met, battery charging can be inhibited by the system 700.

In operation and use, an electrostimulation electronics unit can be provided or obtained, and the electrostimulation electronics unit can include or use first and second neurostimulation output terminals configured for delivering the neurostimulation therapy to a subject, first and second neurostimulation skin electrodes configured to be respectively coupled to the first and second neurostimulation output terminals, and a rechargeable battery. Also, battery charging circuitry can be provided or obtained, and the battery charging circuitry can be capacitively coupled (e.g., coupled using series DC-blocking capacitors, e.g., in a charge-balanced arrangement) via the first and second neurostimulation output terminals for recharging the rechargeable battery. The electrostimulation electronics unit can be charged via the first and second neurostimulation output terminals through the first and second neurostimulation skin electrodes The following, non-limiting examples, detail certain aspects of the present subject matter to solve the challenges and provide the benefits discussed herein, among others.

Example 1 is a transcutaneous neurostimulation therapy system, the system comprising: an electrostimulation electronics unit, including first and second neurostimulation output terminals configured for delivering neurostimulation to a subject via first and second neurostimulation skin electrodes configured to be respectively coupled to the first and second neurostimulation output terminals, the electrostimulation electronics unit including or coupled to a rechargeable battery; and battery charging circuitry configured for being coupled via the first and second neurostimulation output terminals to the electrostimulation electronics unit for charging the battery of the electrostimulation electronics unit through the first and second neurostimulation skin electrodes.

In Example 2, the subject matter of Example 1, wherein the battery charging circuitry is configured for being coupled via the first and second neurostimulation output terminals to the electrostimulation electronics unit for charging the battery.

In Example 3, the subject matter of any of Examples 1-2, further comprising the first and second neurostimulation skin electrodes respectively providing electrical conductivity through a conductive interstitial layer between corresponding first and second neurostimulation output terminals of the electrostimulation electronics unit and the battery charging circuitry.

In Example 4, the subject matter of any of Examples 1-3, wherein the battery charging circuitry is configured to pass electric current across a conductive interstitial polymer layer of the first and second neurostimulation electrodes to charge the battery of the electrostimulation electronics unit.

In Example 5, the subject matter of any of Examples 1-4, wherein the battery charging circuitry includes neurostimulation detection circuitry configured to detect when the neurostimulation is being delivered by the electrostimulation electronics unit and to inhibit charging of the battery when the neurostimulation is being delivered.

In Example 6, the subject matter of Example 5, wherein the battery charging circuitry is configured, in a default state, to deliver a battery charging waveform for charging the battery of the electrostimulation electronics unit: in the absence of the detection of the neurostimulation; and in the absence of a logic state of the electrostimulation electronics unit received or detected by the battery charging circuitry.

In Example 7, the subject matter of any of Examples 1-6, wherein the electrostimulation electronics unit includes neurostimulation inhibition circuitry, configured to inhibit delivering the neurostimulation while charging of the battery is being performed by the battery charging circuitry.

In Example 8, the subject matter of any of Examples 1-7, wherein the battery charging circuitry is configured for charging the battery of the electrostimulation electronics unit without delivering to the electrostimulation electronics unit a battery charging signal that includes a DC component.

In Example 9, the subject matter of any of Examples 1-8, wherein the electrostimulation electronics unit includes an onboard AC-to-DC converter configured to convert an AC battery charging signal received from the battery charging circuitry to a DC battery charging signal to be delivered to the battery.

In Example 10, the subject matter of any of Examples 1-9, wherein the battery charging circuitry is configured for delivering an AC battery charging waveform to the electrostimulation electronics unit.

In Example 11, the subject matter of any of Examples 1-10, wherein the battery charging circuitry is configured for delivering a charge-balanced AC battery charging waveform to the electrostimulation electronics unit.

In Example 12, the subject matter of any of Examples 1-11, wherein the battery charging circuitry includes encoder circuitry for encoding a communication signal onto a battery charging waveform.

In Example 13, the subject matter of Example 12, wherein the encoder includes a modulator.

In Example 14, the subject matter of Example 13, wherein the modulator is configured to modulate waveform frequency.

In Example 15, the subject matter of any of Examples 13-14, wherein the modulator is configured to modulate waveform amplitude.

In Example 16, the subject matter of any of Examples 13-15, wherein the modulator is configured to modulate waveform pulse width.

In Example 17, the subject matter of any of Examples 13-16, wherein the electrostimulation electronics unit includes or is coupled to a modulation receiver.

In Example 18, the subject matter of any of Examples 1-17, further comprising wireless communication circuitry for providing a wireless communication between the electrostimulation electronics unit and the battery charging circuitry.

In Example 19, the subject matter of Example 18, wherein the wireless communication circuitry provides the wireless communication comprising instructions from the battery charging circuitry and received by the electrostimulation electronics unit to inhibit delivering neurostimulation while charging of the battery is being performed by the battery charging circuitry 20. The system of Example 1, wherein the battery charging circuitry is configured to charge the battery without supplying inductive charging.

In Example 20, the subject matter of any of Examples 1-19, further comprising a voltage regulator between the first and second neurostimulation skin electrodes and the battery.

In Example 21, the subject matter of any of Examples 1-20, further comprising a voltage regulator between the first and second neurostimulation skin electrodes and the battery.

In Example 22, the subject matter of any of Examples 1-21, wherein each of the first and second neurostimulation skin electrodes includes or is coupled to: one or more electrical contacts; a hydrophilic polymer layer disposed between the one or more electrical contacts and a patient skin contact surface of the electrode; and electrolyte contained within the hydrophilic polymer layer.

In Example 23, the subject matter of any of Examples 1-22, wherein the battery charging circuitry is configured for delivering an AC battery charging waveform to the electrostimulation electronics unit at a voltage within a range of 20V and 42V.

Example 24 is an electrostimulation electronics unit comprising: first and second neurostimulation output terminals configured for delivering neurostimulation therapy to a subject; first and second neurostimulation skin electrodes configured to be respectively coupled to the first and second neurostimulation output terminals; and a rechargeable battery; wherein the rechargeable battery is configured to be charged via the first and second neurostimulation output terminals capacitively coupled to battery charging circuitry.

Example 25 is an electrostimulation electronics unit docking station comprising: battery charging circuitry configured for being capacitively coupled via first and second neurostimulation output terminals of an electrostimulation electronics unit for charging a battery of the unit via the output terminals.

Example 26 is a method of performing transcutaneous neurostimulation therapy, the method comprising: providing or obtaining an electrostimulation electronics unit; the electrostimulation electronics unit comprising: first and second neurostimulation output terminals configured for delivering the neurostimulation therapy to a subject; first and second neurostimulation skin electrodes configured to be respectively coupled to the first and second neurostimulation output terminals; and a rechargeable battery; providing or obtaining battery charging circuitry, the battery charging circuitry configured for being capacitively coupled via the first and second neurostimulation output terminals for charging the rechargeable battery; capacitively coupling the battery charging circuitry to the electrostimulation electronics unit via the first and second neurostimulation output terminals; and charging the electrostimulation electronics unit via the first and second neurostimulation output terminals.

In Example 26, the subject matter of Example 26, further comprising inhibiting electrostimulation from the first and second neurostimulation output terminals during charging of the rechargeable battery.

Example 28 is at least one machine-readable medium including instructions that, when executed by processing circuitry, cause the processing circuitry to perform operations to implement of any of Examples 1-27.

Example 29 is an apparatus comprising means to implement of any of Examples 1-27.

Example 30 is a system to implement of any of Examples 1-27.

Example 31 is a method to implement of any of Examples 1-27.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described.

However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A transcutaneous neurostimulation therapy system, the system comprising:
   an electrostimulation electronics unit, including first and second neurostimulation output terminals configured for delivering neurostimulation to a subject via first and second neurostimulation skin electrodes configured to be respectively coupled to the first and second neurostimulation output terminals, the electrostimulation electronics unit including or coupled to a rechargeable battery; and
   battery charging circuitry configured for being coupled via the first the first and second neurostimulation skin electrodes and via the first and second neurostimulation output terminals to the electrostimulation electronics unit for charging the battery of the electrostimulation electronics unit through the first and second neurostimulation skin electrodes.

2. The system of claim 1, further comprising the first and second neurostimulation skin electrodes respectively providing electrical conductivity through a conductive interstitial layer between corresponding first and second neurostimulation output terminals of the electrostimulation electronics unit and the battery charging circuitry.

3. The system of claim 1, wherein the battery charging circuitry is configured to pass electric current across a conductive interstitial polymer layer of the first and second neurostimulation electrodes to charge the battery of the electrostimulation electronics unit.

4. The system of claim 1, wherein the battery charging circuitry includes neurostimulation detection circuitry configured to detect when the neurostimulation is being delivered by the electrostimulation electronics unit and to inhibit charging of the battery when the neurostimulation is being delivered.

5. The system of claim 4, wherein the battery charging circuitry is configured, in a default state, to deliver a battery charging waveform for charging the battery of the electrostimulation electronics unit:
in the absence of the detection of the neurostimulation; and
in the absence of a logic state of the electrostimulation electronics unit received or detected by the battery charging circuitry.

6. The system of claim 1, wherein the electrostimulation electronics unit includes neurostimulation inhibition circuitry, configured to inhibit delivering the neurostimulation while charging of the battery is being performed by the battery charging circuitry.

7. The system of claim 1, wherein the battery charging circuitry is configured for charging the battery of the electrostimulation electronics unit without delivering to the electrostimulation electronics unit a battery charging signal that includes a DC component.

8. The system of claim 1, wherein the electrostimulation electronics unit includes an onboard AC-to-DC converter configured to convert an AC battery charging signal received from the battery charging circuitry to a DC battery charging signal to be delivered to the battery.

9. The system of claim 1, wherein the battery charging circuitry is configured for delivering an AC battery charging waveform to the electrostimulation electronics unit.

10. The system of claim 1, wherein the battery charging circuitry is configured for delivering a charge-balanced AC battery charging waveform to the electrostimulation electronics unit.

11. The system of claim 1, wherein the battery charging circuitry includes encoder circuitry for encoding a communication signal onto a battery charging waveform.

12. The system of claim 11, wherein the encoder includes a modulator configured to modulate at least one of the frequency, the amplitude, or the pulse width of the waveform.

13. The system of claim 12, wherein the electrostimulation electronics unit includes or is coupled to a modulation receiver.

14. The system of claim 1, further comprising wireless communication circuitry for providing a wireless communication between the electrostimulation electronics unit and the battery charging circuitry.

15. The system of claim 14, wherein the wireless communication circuitry provides the wireless communication comprising instructions from the battery charging circuitry and received by the electrostimulation electronics unit to inhibit delivering neurostimulation while charging of the battery is being performed by the battery charging circuitry.

16. The system of claim 1, further comprising a voltage regulator between the first and second neurostimulation skin electrodes and the battery.

17. The system of claim 1, wherein the battery charging circuitry is configured to pass electric current across a conductive hydrophilic polymer layer of the first and second neurostimulation electrodes to charge the battery of the electrostimulation electronics unit.

18. The system of claim 1, wherein the battery charging circuitry is configured for being capacitively coupled via the first the first and second neurostimulation skin electrodes and via the first and second neurostimulation output terminals to the electrostimulation electronics unit for charging the battery.

19. A method of performing transcutaneous neurostimulation therapy, the method comprising:
providing or obtaining an electrostimulation electronics unit;
the electrostimulation electronics unit comprising:
first and second neurostimulation output terminals configured for delivering the neurostimulation therapy to a subject;
first and second neurostimulation skin electrodes configured to be respectively coupled to the first and second neurostimulation output terminals; and
a rechargeable battery;
providing or obtaining battery charging circuitry, the battery charging circuitry configured for being coupled via the first and second neurostimulation output terminals for charging the rechargeable battery;
coupling the battery charging circuitry to the electrostimulation electronics unit via the first the first and second neurostimulation skin electrodes and via the first and second neurostimulation output terminals; and
charging the electrostimulation electronics unit via the first and second neurostimulation output terminals.

20. The method of claim 19, further comprising inhibiting electrostimulation from the first and second neurostimulation output terminals during charging of the rechargeable battery.

21. A transcutaneous neurostimulation therapy system, the system comprising:
an electrostimulation electronics unit, including first and second neurostimulation output terminals configured for delivering neurostimulation to a subject via first and second neurostimulation skin electrodes configured to be respectively coupled to the first and second neurostimulation output terminals, the electrostimulation electronics unit including or coupled to a rechargeable battery; and
battery charging circuitry configured for being coupled via the first the first and second neurostimulation skin electrodes and via the first and second neurostimulation output terminals to the electrostimulation electronics unit for charging the battery of the electrostimulation electronics unit through the first and second neurostimulation skin electrodes;

wherein each of the first and second neurostimulation skin electrodes includes or is coupled to:

one or more electrical contacts;

a polymer layer disposed between the one or more electrical contacts and a patient skin contact surface of the electrode; and electrolyte contained within the polymer layer.

* * * * *